United States Patent [19]

Yoshida et al.

[11] Patent Number: 4,962,031
[45] Date of Patent: Oct. 9, 1990

[54] PROCESS FOR PRODUCING OPTICALLY ACTIVE COMPOUNDS

[75] Inventors: Naoyuki Yoshida; Masakazu Kaneoya; Manabu Uchida; Hiroshi Morita, all of Kanagawa, Japan

[73] Assignee: Chisso Corporation, Osaka, Japan

[21] Appl. No.: 189,163

[22] Filed: May 2, 1988

[30] Foreign Application Priority Data

May 1, 1987 [JP]  Japan ................................. 62-106276

[51] Int. Cl.$^5$ ............................................. C12P 41/00
[52] U.S. Cl. .................................. 435/280; 435/128; 435/142; 435/155; 435/156; 435/157
[58] Field of Search ............... 435/280, 128, 147, 155, 435/156, 157

[56] References Cited

U.S. PATENT DOCUMENTS 4,601,987  7/1986  Klibanov et al. .................... 435/280

FOREIGN PATENT DOCUMENTS 166898  7/1987  Japan .

OTHER PUBLICATIONS

Kirchner et al., J. Am. Chem. Soc., vol. 107, (1985), pp. 7072–7076.
Cambou et al., J. Am. Chem. Soc., vol. 106, (1984), pp. 2687–2692.
Chemical Abstracts, vol. 108, No. 13, Mar. 28, 1988, abstract No. 110871r.
Stokes et al., Tetrahedron Letters, vol. 28, No. 19, (1987), pp. 2091–2094.
Chemical Abstracts, vol. 102, No. 17, Apr. 29, 1985, abstract No. 145631r.
Francalanci et al., J. Org. Chem., vol. 52, (1987), pp. 5079–5082.
Cambou et al., Biotechnology and Bioengineering, vol. 26, (1984), pp. 1449–1454.
The Condensed Chemical Dictionary Tenth Edition, Van Nostrand Reinhold, New York, (1981), p. 294.
Frater, "Stereospezifische Synthese von (+)-(3R,4-R)-4-Methyl-3-heptanol", das Enantiomere eines Pheromons de Kleinen Ulmensplintkäfers (Scolytus multistriatus) Helvetica Chiniica Acta, 62(1979)2829–2832.
Zhou et al, "Stereochemical Control of Yeast Reductions. I. Asymmetric Synthesis of L-Carnitine", J. Am. Chem. Soc., (1983), 105: 5925–5926.

*Primary Examiner*—Christine M. Nucker
*Attorney, Agent, or Firm*—Wenderoth, Lind & Ponack

[57] ABSTRACT

The present invention provides a process for producing optically active compounds by a biochemical method in which specific compounds having hydroxyl groups are reacted with esters in the presence of hydrolases. The compounds have the following general formula:

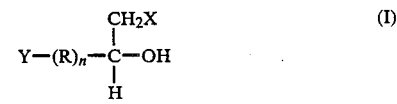

wherein X is selected from halogen atoms and a cyano group. Y is selected from the group constituting substituted phenyl groups, halogen atoms, cyano, trifluoromethyl and amino groups and alkylamino and alkyloxycarbonyl groups in which alkyl groups have 1–20 carbon atoms. R is an alkylene group having 1–20 carbon atoms and n is 0 or 1.

9 Claims, No Drawings

PROCESS FOR PRODUCING OPTICALLY ACTIVE COMPOUNDS

BACKGROUND OF THE INVENTION

The present invention relates to a process for producing optically active compounds in which particular alcohols are reacted with enzymes by a biochemical technique.

Compounds represented by the general formula:

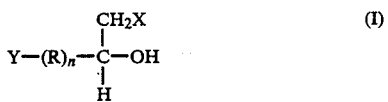

CH2X
Y-(R)n-C-OH  (I)
H are useful chemical compounds as starting materials for pharmaceuticals, agricultural chemicals and the like, and as intermediates. (In formula I, X is selected from halogen atoms, e.g., chlorine, flourine, and bromine, and a cyano group; Y is selected from halogen atoms, e.g., chlorine, flourine, and bromine, a cyano group, a trifluoromethyl group, an amino group, an alkylamino group, an alkyloxycarbonyl group and groups of the following formula:

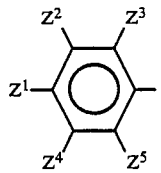

wherein $Z^1$, $Z^2$, $Z^3$, $Z^4$, $Z^5$ are selected from hydrogen and halogen atoms, a cyano group, a trifluoromethyl group, an amino group, an alkylamino group, an aryloxy group, alkyl and alkoxy groups having 1–20 carbon atoms, and groups of the following formula:

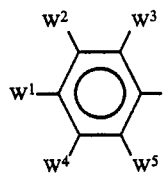

wherein $W^1$, $W^2$, $W^3$, $W^4$ and $W^5$ are selected from hydrogen, halogen atoms, a cyano group, a trifluoromethyl group, an amino group, an alkylamino group, and alkyl and alkoxy groups having 1–20 carbon atoms; and R is an alkylene group having 1–20 carbon atoms; and n is 0 or 1.) However, the compounds have optical isomers, and in many cases they do not sufficiently exhibit their useful characteristics unless the R- or S-alcohol is preponderant.

For the above reasons, and in order to obtain an optically active substance, it is necessary to optically resolve a racemate (itself typically obtained by a synthetic chemical technique), to conduct an asymmetric synthesis, or to convert from an optically active starting material by a stereochemical synthetic method. In many cases, the process is troublesome and disadvantageous industrially.

Accordingly, it is desired to develop a technique for obtaining optically active compounds by an industrially advantageous method.

As a known biochemical technique, for example, there is a method described in Japanese Publication of Unexamined Patent Application No. 59-205989 in which a racemic ester is hydrolyzed with a lipase and a desired alcohol is obtained. In this case, the racemic ester is often insoluble in water, so that it is necessary to emulsify or stir vigorously, using a large quantity of water. Furthermore, as enzyme is water-soluble and unstable to moisture, immobilized enzyme is required so as to act stably and to be easily removed or reused after the reaction.

Klibanov et al. reported a method in which enzyme powder was directly added into a reaction system (J. Am. Chem. Soc., 107, 7072(1985)). In this case, esters for transesterification are extremely limited and 2,2,2-trichloroethyl butyrate is used as the ester. Furthermore, it is essential to use an organic solvent, such as heptane, and ether which has many problems when it is used industrially.

SUMMARY OF THE INVENTION

The inventors of the present invention carried out research for obtaining a process for producing optically active compounds represented by the above general formula (I) by an advantageous industrial method. They found that racemic compounds of raw materials can be efficiently resolved to optically active carboxylic esters and their antipodes, namely optically active alcohols by a biochemical transesterification reaction.

Namely, the present invention provides a process for producing optically active compounds which comprises using a hydrolaze, reacting the.-(R-,S)-alcohol represented by the above general formula (I) and an ester to perform a transesterification reaction under substantially anhydrous conditions, and resolving to an optically active α-halogeno alcohol which contains richly either the R- or S-alcohol and correspondingly the ester of the S- or R-alcohol.

According to the method of the present invention in comparison with conventional methods, the reaction is conducted under anhydrous conditions. This method does not require the use of a small amount of water or a lower alcohol instead of the water, and a side reaction does not occur such as hydrolysis of obtained esters and esters of starting compound and formation of undesirable esters, so that the enzyme is stably kept in organic solvent and easily separated after the reaction and re-used. Furthermore, as the enzyme is directly used and reacted in organic solvent, the method can be kept free from contamination by unwanted microorganisms. Accordingly, there is no necessity for preparing special equipment, antiseptics, sterilization treatment, etc. It is possible to conduct the reaction in an open system. Further, the reaction may be conducted in the same or less quantity of solvent in comparison with common organic synthetic reactions in high substrate concentration.

The following description illustrates this invention more specifically.

In this invention, the (R,S)-alcohols of the raw materials are compounds which are available or can be synthesized.

It is also enough to use esters, preferably triglycerides, which are commercially available without any difficulty. Triacetin, tripropionin, tributyrin tristearin, trilaurin, trimyristin, triolein, etc., can be exemplifies as the triglycerides. As for other esters, methyl propionate, ethyl butyrate, ethyl stearate, trichloroethyl laurate, butyl laurate, ethylene glycol diacetate, etc., can be used.

The hydrolase which is used in this invention has the ability to catalyse a transesterification reaction preferentially between the R- or S-alcohol and the ester when the enzyme is used with the (R,S)-alcohol, and the enzyme can be used regardless its class. For example a lipase, lipoprotein lipase, esterase, etc. are preferable. The following table shows commercially available enzymes that can be used in the present reaction

TABLE

| Trade name | Origin | Seller or Maker |
| --- | --- | --- |
| Lipase AP | Aspergillus niger | Amano Pharmaceutical Co., Ltd |
| Lipase M | Mucor javanicus | Amano Pharmaceutical Co., Ltd |
| Lipase P | Pseudomonas fluorescens | Amano Pharmaceutical Co., Ltd |
| Lipase CES | Pseudomonas sp | Amano Pharmaceutical Co., Ltd |
| Lipase CE | Humicola lanuginosa | Amano Pharmaceutical Co., Ltd |
| Lipase F-AP | Rhizopus javanicus | Amano Pharmaceutical Co., Ltd |
| Lipase II | Porcine pancreas | Sigma Chemical Co., Ltd |
| Lipase VIII | Geotrichum candidum | Sigma Chemical Co., Ltd |
| Lipase X | Rhizopus delamar | Sigma Chemical Co., Ltd |
| Lipase | Chromobacterium viscosum | Toyo Jozo Co., Ltd |
| Palatase A | Aspergillis niger | Novo Industi A/S |
| Lipase | Rhizopus niveus | Nagase Biochemicals, Co. Ltd |

In addition to these enzymes, microorganisms which produce the enzymes having the above ability can be used regardless of their species and genus. As such microorganisms, the genera *Arthrobacter, Acromobacter, Alcaligenes, Aspergillus, Chromobacterium, Candida, Mucor, Pseudomonas, Rhizopus*, etc., can be exemplified. The enzymes produced from these microorganisms can be also used.

In practice of the present invention, (R,S-alcohols and esters such as triglycerides can be used without any particular treatments.

The reaction is typically conducted by mixing an (R,S)-alcohol with an ester, preferably a triglyceride, if necessary adding an organic solvent such as heptane or toluene when the alcohol is slightly soluble in the ester, and contacting efficiently the mixture with an enzyme.

The reaction temperature is suitably 20° to 70° C. and especially preferably 30° to 45° C. The reaction time is widely variable, say 5 to 2000 hours. The reaction time can be shortened by elevating the reaction temperature or using an enzyme having high activity (large numbers of units) or lowering the substrate concentration.

The (R,S)-alcohol which is a substrate and the ester are suitably mixed in the ratio 1:0.5 to 1:2 by mole, and preferably 1:1.1 to 1:1.5 by mole.

After the transesterification reaction, the enzyme can be removed by conventional filter operation and used again, as it is. The filtrate can be separated into an optically active alcohol and an ester, respectively, for instance by distillation or column chromatography. The obtained ester is hydrolyzed in an alkali or acid solution to derive the optically active alcohol which is an antipode of the above alcohol.

By the above described process, the optically active R- and S-alcohol can be obtained.

The merits of this invention are as follows. (1) Unnecessary hydrolysis of esters scarcely occurs because the transesterification reaction is substantially conducted under the conditions of no water. (2) The enzyme can be easily recovered and re-used. (3) No special equipment and materials are used because the reaction can be performed under the conditions of relatively lower temperatures and an open system. (4) Optically active substances having high purity are obtained by a one-step reaction. (5) In spite of the biochemical reaction, the substrate concentration can be increased and big reaction vessels are unnecessary, because a buffer solution and the like are not required in the reaction.

DESCRIPTION OF PREFERRED EMBODIMENTS

The following examples illustrate this invention more specifically.

Example 1

Sixteen grammes of enzyme (produced by Amano pharmaceutical Co. Ltd., Lipase "Amano CES"), 7.9g (0.05mol) of (R,S)-2-chloro-1-phenylethanol and 17.8g (0.059mol) of tributyrin were charged into three-necked flask and reacted with stirring for 16days at 35° C. After the reaction was stopped, the enzyme was removed by filtration, the filtrate was concentrated by distillation under reduced pressure, and the desired compounds were isolated by column chromatography. As the result, 4.0g of (R)-2-chloro-1-phenylethanol (yield: 50%, 58% ee) and (S)-2-chloro-1-phenylethyl butyrate were obtained. The obtained (S)-2-chloro-1-phenylethyl butyrate was hydrolyzed in an acidic solution of hydro chloric acid, and (S)-2-chloro-1-phenylethanol (yield: 23%, >99% ee) was obtained. Optical purity of the obtained compounds was determined by HPLC of optical resolution.

The obtained compounds were identified by structure analysis with NMR.

Example 2

Ten grammes of enzyme (produced by Amano pharmaceutical Co. Ltd., Lipase "Amano CES"), 16.7g (0.1 mol) of (R,S)-ethyl 4-chloro-3-hydroxybutyrate and 33.3g (0.11 mol) of tributyrin were charged into three-necked flask and reacted with stirring for 12 days at 35° C. After the reaction was stopped, the enzyme was removed by filtration and 7g of (R)-ethyl 4-chloro-3-hydroxybutyrate ($[\alpha]_D = +3.0°$ (cl.02 , CHCl$_3$)) was obtained by distillation from the filtrate.

Example 3

Using the same method as described in Example 2, (R,S)-tert-butyl 4-chloro-3-hydroxybutyrate was resolved.

R-(+)-tert-butyl 4-chloro-3-hydroxybutyrate ($[\alpha]_D^{24.5}$ +8.2° (cl.0, CHCl$_3$)) and S-(−)-tert-butyl 3-butyryloxy-4-chlorobutyrate ($[\alpha]_D^{26}$ —separated.

A compound of Example 1 of the formula

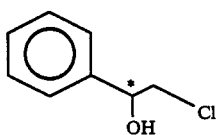

is useful as an intermediate in the preparation of a compound of the formula

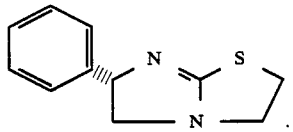

See Katsuki et al., Nippon Hakko Kogyokai (Japanese Fermentation Industry Association) mass meeting, Collection of Lecture Points, page 106, 1986).

The compounds of Examples 2 and 3 are useful as intermediates as follows:

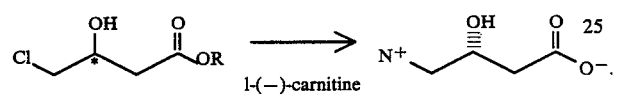

See Ann. New York Acad. Sci., 1984, 186, C. J. Sih et al.

What is claimed is:

1. A process for producing an optically active compound which comprises reacting under substantially anhydrous conditions and in the presence of lipase obtained from a *Pseudomonas* species, a triglyceride and an (R,S)-compound represented by the general formula (I):

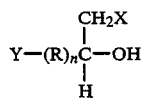

wherein
X is a member selected from the group consisting of chlorine, bromine and fluorine,
Y is a member selected from the group consisting of chlorine, bromine, fluorine, cyano, alkyloxycarbonyl in which the alkyl moiety is of 1-20 carbon atoms and
a group of the following formula:

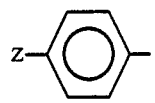

wherein Z is hydrogen, halogen, alkyl of 1-20 carbon atoms, alkoxy of 1-20 carbon atoms or a group of the following formula:

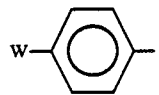

wherein W is alkyl of 1-2 carbon atoms or alkoxy of 1-20 carbon atoms,
R is alkylene of 1-20 carbon atoms; and
n is 0 or 1,
to effect a transesterification reaction, and resolving to an optically active α-halogeno alcohol which has either the R- or S-configuration and the corresponding ester of the S- or R-alcohol.

2. A process as claimed in claim 1, wherein the triglyceride is tributyrin.

3. A process as claimed in claim 1, wherein Y is a phenyl group, and n is 0.

4. A process as claimed in claim 1 wherein X is chlorine.

5. A process as claimed in claim 1, wherein the (R,S)-compound represented by the formula (I) is (R,S),-2-chloro-1-phenylethanol.

6. A process as claimed in claim 1, wherein Y is an alkyloxycarbonyl group, and R is a methylene group.

7. A process as claimed in claim 1, wherein the (R,S)-compound represented by the formula (I) is (R,S)-ethyl 4-chloro-3-hydroxybutyrate or (R,S)-t-butyl 4-chloro-3-hydroxybutyrate.

8. A process as claimed in claim 2, wherein the (R,S)-compound represented by the formula (I) is (R,S)-2-chloro-1-phenylethanol.

9. A process as claimed in claim 2 wherein Y is a phenyl group, and n is 0.

* * * * *